United States Patent [19]
Gans

[11] Patent Number: 5,908,838
[45] Date of Patent: Jun. 1, 1999

[54] METHOD FOR THE TREATMENT OF ACNE

[75] Inventor: Eugene H. Gans, Phoenix, Ariz.

[73] Assignee: Medics Pharmaceutical Corporation, Phoenix, Ariz.

[21] Appl. No.: 09/028,871

[22] Filed: Feb. 19, 1998

[51] Int. Cl.$^6$ .................................................. A61K 31/65

[52] U.S. Cl. ............................................... 514/152

[58] Field of Search ............................................. 514/152

[56] References Cited

U.S. PATENT DOCUMENTS 5,518,730  5/1996  Fuisz ........................................ 424/426

OTHER PUBLICATIONS

Williams et al., the Lancet, 2(7883) 744–6 Sep. 28, 1974.

*Primary Examiner*—Phyllis Spivack
*Attorney, Agent, or Firm*—William J. McNichol, Jr.

[57] ABSTRACT

A method for the treatment of acne is provided which results in the reduction of vestibular side effects following administration of oral tetracycline antibiotics.

18 Claims, No Drawings

METHOD FOR THE TREATMENT OF ACNE

FIELD OF THE INVENTION

This invention relates to methods for the treatment of acne, and in particular to methods for the treatment of acne involving the use of oral tetracycline antibiotics.

BACKGROUND OF THE INVENTION

Oral tetracycline antibiotics are frequently used in the treatment of acne. One of the most effective oral tetracycline antibiotics used in the treatment of acne it is minocycline. All tetracycline antibiotics are known to have some side effects. These side effects include vestibular symptoms such as vertigo, dizziness or blurred vision. These effects are sometimes disabling. See, Gould & Brookler, Arch. Otolarang. Vol. 96, p. 291 (1972); Williams et al., Lancet, Sep. 28, 1974, p. 144–45; Fanning & Gump, Arch. Intern. Med., Vol. 136, pp. 761–62 (1976). Headache and general malaise, along with gastro-intestinal symptoms such as the diarrhea, nausea, gas, or cramps also occur. Dry nose and dry mouth are also occasionally encountered.

Dosage forms of oral tetracycline antibiotics are typically constructed with a view towards achieving rapid dissolution rates. Rapid dissolution is believed to be essential to the effectiveness of these drugs. The driving force behind this practice is the understanding that rapid dissolution leads to rapid assimilation through the gut lining, where the antibiotics are then transmitted through the blood stream to the skin, where they are active against bacteria associated with acne. The U.S. Food and Drug Administration (FDA) has established standards for dissolution rates for various oral antibiotics. These standards set minimum dissolution rates. For example, the FDA standard for oral minocycline is that 75 percent of the stated dosage must have dissolved within 45 minutes, under standard U.S. Pharmacopea test conditions. Commercial products are typically engineered to have a dissolution rates which are substantially faster than that required by the FDA. All of this is based upon the generally accepted belief in the art that, while dissolution rates enhance the effectiveness of the antibiotic, once the FDA minimum dissolution rate is achieved, all products have equivalent safety and efficacy.

SUMMARY OF THE INVENTION

It has been discovered that the dissolution rate of oral tetracycline antibiotics, especially minocycline, can affect the occurrence of vestibular side effects. Specifically, too rapid dissolution of oral tetracyclines increases the incidence and severity of vestibular side effects. By reducing or slowing the dissolution rates of the antibiotics, the incidence and/or severity of vestibular side effects can be reduced significantly.

DETAILED DESCRIPTION OF THE INVENTION

Vestibular reactions are an undesirable and sometimes seriously disconcerting side effect of minocycline therapy. According to the present invention, it is possible to provide persons susceptible to such side effects with the benefits of minocycline therapy while diminishing the incidence and/or severity of these side effects. This is accomplished by adjusting the dissolution rate of the minocycline in its dosage form so that, while an effective concentration of minocycline is achieved in the blood stream of the patient, vestibular side effects are greatly reduced.

In a preferred embodiment of the invention, the minocycline dissolves at a rate of only 15 percent within the first 15 minutes, 35 percent within 30 minutes, 50 percent within 45 minutes, and 80 percent within one hour. It is also advantageous to use a dissolution rate of 20 percent within 15 minutes, 50 percent in 30 minutes, 75 percent within 45 minutes and 100 percent dissolution within 60 minutes. Dissolution rates as fast as 30 percent within 15 minutes, 60 percent within 30 minutes, 75 percent within 45 minutes and complete dissolution within 60 minutes or even as fast as 35 percent within 15 minutes, 80 percent within 30 minutes and substantially complete dissolution within 45 minutes can be used. Preferred dissolution rates are within the range of 20 to 40 percent in 15 minutes, 50 to 80 percent in 30 minutes, and 70 to 95 percent in 45 minutes. Faster rates of 25 to 35 percent in 15 minutes, 60 to 80 percent in 30 minutes and 80 to 100 percent in 45 minutes are useful. It will be understood however, that the faster dissolution rates do not achieve as significant a reduction in the reduction of unwanted side effects as the slower dissolution rates.

Minocycline is available from a variety of sources. Various commercial products containing minocycline as their active ingredient have a variety of the dissolution rates. In the following example, slower dissolving minocycline is compared with fast-dissolving minocycline.

A blinded cross-over study of the vestibular side effects of minocycline involving 32 female subjects was conducted. The subjects were given either a fast dissolving or a slower dissolving dosage form of minocycline. The doses for the subjects were adjusted on the basis of each subject's total body weight and were in the range typically used for the treatment of severe acne. Subjects weighing 50 to 69 kg were given one-hundred milligrams. Subjects weighing 70 to 89 kg, the dose were given one hundred fifty milligrams and subjects above received 90 kilograms, 200 milligrams. This dose was given once a day at 5 p.m. Subjects received one of the two dose forms for four days. After a two week washout, each group "crossed over" and received the dosage form that they had not received during the first four day period. Each subject was required to maintain an accurate diary of vestibular side effects. The diary recorded the number of days that each subject experienced vestibular side effects and the number of incidents of each symptom. The 32 subjects were evaluated over a five day period, yielding 160 person-day measurements per treatment group. The number of days that each subject recorded a side effect and the severity of that side effect the reported in Table 1.

From Table 1 it can be seen that a total of 27 incidents of vestibular side effects occurred in the fast dissolving treatment group, compared to only five incidents in the slower dissolving group. The severity of the vestibular side effects are reported on a scale of 1 to 4. With 1 indicating slight severity, 2 indicating mild severity, 3 moderate, and 4 severe side effects.

The dissolution rates for the fast dissolving dosage form and the slower dissolving dosage form are set forth below.

TABLE 1

| Symptom | Severity | No. of Time Intervals | Duration | Severity Category |
|---|---|---|---|---|
| Patients Treated With Slower-Dissolving Minocycline ||||| 
| dizziness | slight | 2 | 8:00 am–4:00 pm | 1 |
| dizziness | slight-mild | 4 | all day | 1.5 |
| dizziness | mild | 1 | on and off | 2 |
| dizziness | slight | 1 | all evening | 1 |

TABLE 1-continued

| Symptom | Severity | Vestibular Side Effects No. of Time Intervals | Duration | Severity Category |
|---|---|---|---|---|
| dizziness | slight-mild | 2 | morning thru mid day | 1.5 |
| Patients Treated With Fast-Dissolving Minocycline ||||
| dizziness | slight | 2 | 7:00 am–12:00 pm | 1 |
| blurred vision | slight-mild | 2 | 8:00 am–3:00 pm | 1.5 |
| dizziness | slight | 2 | 7:00 am–12:00 pm | 1 |
| dizziness | slight | 2 | 8:00 am–2:00 pm | 1 |
| dizziness | slight | 2 | 7:00 am–2:00 pm | 1 |
| dizziness | slight | 2 | 7:00 am–3:00 pm | 1 |
| dizziness | slight | 2 | morning-late afternoon | 1 |
| dizziness | slight | 2 | morning-late afternoon | 1 |
| dizziness | slight | 2 | morning-late afternoon | 1 |
| dizziness | slight | 1 | 1 hour | 1 |
| dizziness | slight | 1 | 2 hours | 1 |
| dizziness | slight | 1 | about 1–2 hours | 1 |
| dizziness | slight | 1 | about 1.5 hours | 1 |
| dizziness | slight | 1 | 2 hours | 1 |
| blurred vision | slight | 1 | 1 hour | 1 |
| dizziness | slight | 1 | 2 hours | 1 |
| dizziness | slight-mild | 2 | 7.5 hours | 1.5 |
| dizziness | mild | 1 | 6:00 am–8:00 am | 2 |
| vertigo | mild | 1 | 2:00 am–8:00 am | 2 |
| dizziness | mild | 1 | 6:00 am–8:00 am | 2 |
| vertigo | mild | 1 | 2:00 am–8:00 am | 2 |
| dizziness | mild | 1 | 6:00 am–8:00 am | 2 |
| vertigo | mild | 1 | 6:00 am–8:00 am | 2 |
| dizziness | mild | 1 | 6:00 am–8:00 am | 2 |
| vertigo | mild | 1 | 6:00 am–8:00 am | 2 |
| dizziness | mild | 1 | 6:00 am–8:00 am | 2 |
| vertigo | mild | 1 | 6:00 am–8:00 am | 2 |

TABLE 2

| Fast Dissolving || Slow Dissolving ||
| Time (Min.) | % Dissolution | Time (Min.) | % Dissolution |
|---|---|---|---|
| 0 | 0.0 | 0 | 0.0 |
| 15 | 100 | 15 | 30 |
| 30 | 100 | 30 | 67 |
| 45 | 100 | 45 | 88 |
| 60 | 100 | 60 | 95 |

The cause of the effectiveness of this invention is not known. However, it can be speculated that the dissolution rates called for by the present invention allow the vestibular organs to acclimate themselves to the presence of the minocycline, and thereby avoid unwanted side effects. This explanation is consistent with the avoidance of vestibular side effects even through the use of both slow and fast dissolving dosage forms may achieve the same level of minocycline in the blood stream.

The foregoing example is given by way of illustration only. The scope of the invention is defined only by the following claims.

I claim:

1. A method for reducing the incidence or severity of vestibular side effects resulting from the treatment of acne by the use of oral tetracycline antibiotics, comprising administering the oral tetracycline antibiotic in a slowly dissolving dosage form.

2. The method of claim 1, wherein the oral tetracycline antibiotic is minocycline.

3. The method of claim 2, wherein the antibiotic dissolves at a rate no faster than 15 percent in 15 minutes, 35 percent in 30 minutes, 50 percent in 45 minutes and 80 percent in 60 minutes.

4. The method of the claim 2 wherein the antibiotic dissolves at a rate no faster than 20 percent in 15 minutes, 50 percent in 30 minutes, and 75 percent in 45 minutes.

5. The method of claim 2 wherein and the antibiotic dissolves at a rate no faster than 30 percent in 15 minutes, 60 percent in 30 minutes, and 75 percent in 45 minutes.

6. The method of the claim 2 wherein the antibiotic dissolves at a rate no faster than 35 percent in 15 minutes, 80 percent in 30 minutes, and one hundred percent in 45 minutes.

7. The method of claim 2, wherein the antibiotic dissolves at a rate within the range of 20 to 40 percent in 15 minutes, 50 to 80 percent in 30 minutes, 70 to 95 percent in 45 minutes and 95 to 100 percent in 60 minutes.

8. The method of the claim 2 wherein the antibiotic dissolves at a rate within the range of 25 to 35 percent in 15 minutes, 60 to 80 percent in 30 minutes, and 80 to 100 percent in 45 minutes.

9. The method of claim 2 wherein and the antibiotic dissolves at a rate within the range of 30 to 35 percent in 15 minutes, 65 to 75 percent in 30 minutes, and 90 to 100 percent in 45 minutes.

10. A method for reducing the incidence or severity of vestibular side effects resulting from the treatment of acne by the use of oral tetracycline antibiotics, comprising administering the oral tetracycline antibiotic in a slowly dissolving dosage form, wherein the dissolution of the antibiotic is substantially complete in less than 24 hours.

11. The method of claim 10, wherein the oral tetracycline antibiotic is minocycline.

12. The method of claim 11, wherein the antibiotic dissolves at a rate no faster than 15 percent in 15 minutes, 35 percent in 30 minutes, 50 percent in 45 minutes and 80 percent in 60 minutes.

13. The method of claim 11 wherein the antibiotic dissolves at a rate no faster than 20 percent in 15 minutes, 50 percent in 30 minutes, and 75 percent in 45 minutes.

14. The method of claim 11 wherein and the antibiotic dissolves at a rate no faster than 30 percent in 15 minutes, 60 percent in 30 minutes, and 75 percent in 45 minutes.

15. The method of claim 11 wherein the antibiotic dissolves at a rate no faster than 35 percent in 15 minutes, 80 percent in 30 minutes, and one hundred percent in 45 minutes.

16. The method of claim 11, wherein the antibiotic dissolves at a rate within the range of 20 to 40 percent in 15 minutes, 50 to 80 percent in 30 minutes, 70 to 95 percent in 45 minutes and 95 to 100 percent in 60 minutes.

17. The method of claim 11 wherein the antibiotic dissolves at a rate within the range of 25 to 35 percent in 15 minutes, 60 to 80 percent in 30 minutes, and 80 to 100 percent in 45 minutes.

18. The method of claim 11 wherein and the antibiotic dissolves at a rate within the range of 30 to 35 percent in 15 minutes, 65 to 75 percent in 30 minutes, and 90 to 100 percent in 45 minutes.

* * * * *

UNITED STATES PATENT AND TRADEMARK OFFICE
CERTIFICATE OF CORRECTION

PATENT NO. : 5,908,838 C1  Page 1 of 1
APPLICATION NO. : 90/009180
DATED : June 1, 2010
INVENTOR(S) : Eugene H. Gans It is certified that error appears in the above-identified patent and that said Letters Patent is hereby corrected as shown below:

Title Pg, Item (73), Assignee: delete "Norwest Bank Arizona, National Association, Tempe, AZ (US)" and insert --Medicis Pharmaceutical Corporation, Scottsdale, AZ (US)-- therefor.

Signed and Sealed this

Twelfth Day of October, 2010

David J. Kappos
*Director of the United States Patent and Trademark Office*

(12) EX PARTE REEXAMINATION CERTIFICATE (7540th)
United States Patent
Gans

(10) Number: US 5,908,838 C1
(45) Certificate Issued: Jun. 1, 2010

(54) METHOD FOR THE TREATMENT OF ACNE

(75) Inventor: Eugene H. Gans, Phoenix, AZ (US)

(73) Assignee: Norwest Bank Arizona, National Association, Tempe, AZ (US)

Reexamination Request:
No. 90/009,180, Jun. 24, 2008

Reexamination Certificate for:
Patent No.: 5,908,838
Issued: Jun. 1, 1999
Appl. No.: 09/028,871
Filed: Feb. 19, 1998

(51) Int. Cl.
*A61K 31/65* (2006.01)

(52) U.S. Cl. .................................................. 514/152
(58) Field of Classification Search ................... None
See application file for complete search history.

(56) References Cited

U.S. PATENT DOCUMENTS

| | | |
|---|---|---|
| 3,932,615 A | 1/1976 | Ito et al. |
| 3,957,980 A | 5/1976 | Noseworthy |
| 3,966,922 A | 6/1976 | Okamoto et al. |
| 4,086,332 A | 4/1978 | Armstrong |
| 4,126,680 A | 11/1978 | Armstrong |
| 4,369,172 A | 1/1983 | Schor et al. |
| 4,376,118 A | 3/1983 | Daher et al. |
| 4,443,442 A | 4/1984 | Skillern |
| 4,701,320 A | 10/1987 | Hasegawa et al. |
| 4,764,377 A | 8/1988 | Goodson |
| 4,792,448 A | 12/1988 | Ranade |
| 4,806,529 A | 2/1989 | Levy |
| 4,837,030 A | 6/1989 | Valorose, Jr. et al. |
| 4,925,833 A | 5/1990 | McNamara et al. |
| 4,935,411 A | 6/1990 | McNamara et al. |
| 4,935,412 A | 6/1990 | McNamara et al. |
| 4,960,913 A | 10/1990 | Szalay et al. |
| 5,007,790 A | 4/1991 | Shell |
| 5,122,519 A | 6/1992 | Ritter |
| 5,167,964 A | 12/1992 | Muhammad et al. |
| 5,188,836 A | 2/1993 | Muhammad et al. |
| 5,202,128 A | 4/1993 | Morella et al. |
| 5,209,978 A | 5/1993 | Kosaka et al. |
| 5,211,958 A | 5/1993 | Akkerboom et al. |
| 5,217,493 A | 6/1993 | Raad et al. |
| 5,230,895 A | 7/1993 | Czarniceki et al. |
| 5,262,173 A | 11/1993 | Sheth et al. |
| 5,277,916 A | 1/1994 | Dwyer et al. |
| 5,283,065 A | 2/1994 | Doyon et al. |
| 5,300,304 A | 4/1994 | Sheth et al. |
| 5,324,751 A | 6/1994 | DuRoss |
| 5,348,748 A | 9/1994 | Sheth et al. |
| 5,413,777 A | 5/1995 | Sheth et al. |
| 5,459,135 A | 10/1995 | Golub et al. |
| 5,518,730 A | 5/1996 | Fuisz |
| 5,554,654 A | 9/1996 | Yu et al. |
| 5,582,837 A | 12/1996 | Shell |
| 5,665,776 A | 9/1997 | Yu et al. |
| 5,674,539 A | 10/1997 | Tomas |
| 5,776,489 A | 7/1998 | Preston et al. |
| 5,780,049 A | 7/1998 | Dickner et al. |
| 5,800,836 A | 9/1998 | Morella et al. |
| 5,814,331 A | 9/1998 | Holen |
| 5,834,450 A | 11/1998 | Su |
| 5,855,904 A | 1/1999 | Chung et al. |
| 5,908,838 A | 6/1999 | Gans |
| 5,972,389 A | 10/1999 | Shell et al. |
| 6,087,382 A | 7/2000 | Bonner, Jr. et al. |
| 6,120,803 A | 9/2000 | Wong et al. |
| 6,165,513 A | 12/2000 | Dansereau et al. |
| 6,165,999 A | 12/2000 | Vu |
| 6,194,000 B1 | 2/2001 | Smith et al. |
| 6,340,475 B2 | 1/2002 | Shell et al. |
| 6,340,476 B1 | 1/2002 | Midha et al. |
| 6,399,652 B1 | 6/2002 | Parks |
| 6,429,204 B1 | 8/2002 | Golub et al. |
| 6,455,583 B1 | 9/2002 | Pflugfelder et al. |
| 6,497,902 B1 | 12/2002 | Ma |
| 6,638,922 B2 | 10/2003 | Ashley et al. |
| 6,673,843 B2 | 1/2004 | Arbiser |
| 6,863,830 B1 | 3/2005 | Purdy et al. |
| 6,958,161 B2 | 10/2005 | Hayes et al. |
| 7,008,631 B2 | 3/2006 | Ashley |
| 7,211,267 B2 | 5/2007 | Ashley |
| 7,541,347 B2 | 6/2009 | Wortzman |
| 7,544,373 B2 | 6/2009 | Wortzman |
| 2002/0015731 A1 | 2/2002 | Appel et al. |
| 2003/0082120 A1 | 5/2003 | Milstein |
| 2003/0130240 A1 | 7/2003 | Ashley |
| 2003/0139380 A1 | 7/2003 | Ashley |
| 2003/0199480 A1 | 10/2003 | Hayes et al. |
| 2003/0229055 A1 | 12/2003 | Ashley |
| 2004/0002481 A1 | 1/2004 | Ashley et al. |
| 2004/0115261 A1 | 6/2004 | Ashley |
| 2004/0127471 A1 | 7/2004 | Reisberg |
| 2004/0228912 A1 | 11/2004 | Chang et al. |
| 2005/0136107 A1 | 6/2005 | Patel et al. |
| 2005/0148552 A1 | 7/2005 | Ryan et al. |
| 2006/0293290 A1 | 12/2006 | Wortzman |
| 2007/0254855 A1 | 11/2007 | Wortzman et al. |
| 2007/0259039 A1 | 11/2007 | Wortzman et al. |
| 2007/0270390 A1 | 11/2007 | Wortzman et al. |
| 2007/0275933 A1 | 11/2007 | Wortzman et al. |
| 2008/0070872 A1 | 3/2008 | Wortzman et al. |
| 2008/0241197 A1 | 10/2008 | Wortzman |
| 2008/0241235 A1 | 10/2008 | Wortzman |
| 2008/0241236 A1 | 10/2008 | Wortzman et al. |
| 2008/0241241 A1 | 10/2008 | Wortzman |
| 2008/0242641 A1 | 10/2008 | Wortzman et al. |
| 2008/0242642 A1 | 10/2008 | Wortzman |

FOREIGN PATENT DOCUMENTS

CA 2068366 A1 11/1992

(Continued)

OTHER PUBLICATIONS

Edward R. Barnhart (publisher); MINOCIN®: Minocycline Hydrochloride for Oral use; Physicians' Desk Reference; 1989; pp. 1134–1136; 43rd ed.; Medical Economics Co. Inc.; Oradell, NJ.

(Continued)

*Primary Examiner*—Gary L Kunz

(57) ABSTRACT

A method for the treatment of acne is provided which results in the reduction of vestibular side effects following administration of oral tetracycline antibiotics.

FOREIGN PATENT DOCUMENTS

| CA | 2025703 C | 8/2002 |
| --- | --- | --- |
| CA | 2090561 C | 10/2004 |
| EP | 0 184 389 A2 | 6/1986 |
| EP | 0 418 565 A2 | 3/1991 |
| EP | 0 558 913 A1 | 9/1993 |
| GB | 2414668 A | 12/2005 |
| JP | 02006437 A | 1/1990 |
| WO | WO 93/18755 A1 | 9/1993 |
| WO | WO 98/11879 A1 | 3/1998 |
| WO | WO 98/55107 A1 | 12/1998 |
| WO | WO 99/58131 A1 | 11/1999 |
| WO | WO 02/080932 A1 | 10/2002 |
| WO | WO 03/088906 A2 | 10/2003 |
| WO | WO 2004/012700 A2 | 2/2004 |
| WO | WO 2004/078111 A2 | 9/2004 |

OTHER PUBLICATIONS

AAI International Procore® and Prosorb® Technology, referencing patents issued prior to 2000.

Gilbert et al., Extended–Release Minocycline: Is Efficacy Dose–dependent in the Approved Dose Range?, Poster Presentation for the DUSA Pharmaceuticals, Inc. Medical Conferences and Trade Shows, Hawaii, Mar. 3–9, 2007.

"Is minocycline overused in acne?" Drug and Therapeutics Bulletin. vol. 44 No. 8, 60–62, Aug. 2006.

Prescribingreference.com, Prescribing Reference, Drug News—Minocin PAC for Acne (Oct. 11, 2006).

Eugene L. Parrott, Pharmaceutical Technology: Fundamental Pharmaceutics 92–99 (1970).

Pharmaceutical Dosage Forms Tablets 108–9, 149–51 (Herbeli A. Lieberman & Leon Lachman eds.) (vol. 3 1982).

Goodman and Gilman's The Pharmacological Basis of Therapeutics 1120–1122 (Alfred Goodman Gilman et al. eds.) (1990).

Remington: The Science and Practice of Pharmacy 1310–11, 1662–1675 (19th ed. 1995).

Healey et al. (1994) "Fortnightly Review Acne Vulgaris" BMJ 308: 831–833.

In the United States District Court for the District of Delaware, C.A. No. 09–33 (JJF) (Consolidated), *Medicis Pharmaceutical Corporation v. Mylan Inc., Matrix Laboratories Ltd., Ranbaxy Inc. and Ranbaxy Laboratories Ltd.*: Rabaxy Inc.'s and Ranbaxy Laboratories Ltd.'s Supplemental Responses to Medicis' First Set of Interrogatories (Nos. 1–8), Oct. 23, 2009.

In the United States District Court for the District of Delaware, C.A. No. 09–33 (JJF) (Consolidated), *Medicis Pharmaceutical Corporation v. Mylan Inc., Matrix Laboratories Ltd., Ranbaxy Inc. and Ranbaxy Laboratories Ltd.*: Second Supplemental Response of Mylan Inc. and Matrix Laboratories Ltd. to Plaintiff's Interrogatory No. 3 to all Defendants, Oct. 23, 2009.

Del Rosso, J.Q., "What's new in the Medicine Cabinet?", Supplement to the Feb. 2005 Skin and Aging Conference, pp. 3–6.

Thiboutot, "Hormonal Therapy and Acne," Supplement to the Feb. 2005 Skin and Aging Conference, pp. 7–9.

Berson, D.S., "Acne Update: Treating Female Patients", Supplement to the Feb. 2005 Skin and Aging Conference, pp. 10–12.

Bikowski, J.B., "New Approaches to Rosacea Therapy", Supplement to the Feb. 2005 Skin and Aging Conference, pp. 13–15.

Lebwohl, M. "Management of Problem Psoriasis", Supplement to the Feb. 2005 Skin and Aging Conference, pp. 16–18.

Eichenfield, L.F., "New Developments in Pediatric Dermatology", Supplement to the Feb. 2005 Skin and Aging Conference, pp. 19–20.

Eichenfield, L.F., "Advances in Topical Immunomodulators", Supplement to the Feb. 2005 Skin and Aging Conference, pp. 21–22.

Zane, L.T., "Welcome to the Next Generation of Acne Research", Seminars in Cutaneous Medicine and Surgery, Jun. 2005, vol. 24, No. 2, pp. 65–66.

Bruggemann, H., "Insights in the Pathogenic Potential of Propionibacterium Acnes From It's Complete Genome", Seminars in Cutaneous Medicine and Surgery, Jun. 2005, vol. 24, No. 2, pp. 67–72.

McInturff J.E., et al., "The Role of Toll–Like Receptors in the Pathophysiology of Acne", Seminars in Cutaneous Medicine and Surgery, Jun. 2005, vol. 24, No. 2, pp. 73–78.

Holland, D.B., et al., "The Role of Inflammation in the Pathogenesis of Acne and Acne Scarring", Cutaneous Medicine and Surgery, Jun. 2005, vol. 24, No. 2, pp. 79–83.

Cordain, L., "Implications for the Role of Diet in Acne", Cutaneous Medicine and Surgery, Jun. 2005, vol. 24, No. 2, pp. 84–91.

Marqueling, A.L., "Depression and Suicidal Behavior in Acne Patients Treated with Isotretinoin: A Systematic Review", Cutaneous Medicine and Surgery, Jun. 2005, vol. 24, No. 2, pp. 92–102.

Harper, J.C., "Hormonal Therapy for Acne Using Oral Contraceptive Pills", Cutaneous Medicine and Surgery, Jun. 2005, vol. 24, No. 2, pp. 103–106.

Bhardwaj, S.S., "Lasers and Light Therapy for Acne Vulgaris", Cutaneous Medicine and Surgery, Jun. 2005, vol. 24, No. 2, pp. 107–112.

Solodyn® The Next Generation, © 2008 Medicis, 6 pages.

ABPI Compendium of Data Sheets and Summaries of Product Characteristics 1996–97, Wyeth Laboratories 1244–1245.

Ad Hoc Committee Report: Systemic Antibiotics for Treatment of Acne Vulgaris, Antibiotics and Acne Committee Report, Arch. Dermatology, 1975, 111, p. 163–1636.

Allen, "Minocycline," Diagnosis and Treatment—Drugs Five Years Later, Annals of Internal Medicine, 1976, 85, 482–487.

Bauer, "Investigation Report Concerning Minocycline," Albert–Ludwigs–Universitat, Sep. 1993, 7 pages.

Cohlan, et al., "Growth Inhibition of Prematures Receiving Tetracycline," American Journal of Diseases of Children, 1963, 105, p. 453–461.

Colucci, USP Dissolution Testing Results, Oct. 25, 1993, 9 pages.

Cullen, et al., "Minocycline Therapy in Acne Volgaris," Cutaneous Medicine for the Practitioner, Jun. 1976, 17, 6, 1208–1214.

Cullen, "Low Dose Minocycline Therapy in Tetracycline–Recalcitrant Acne Vulgaris," Cutaneous Medicine for the Practitioner, 1978, 21, 1, 101–106.

Fanning, et al., "Distressing Side–Effects of Minocycline Hydrochloride," 2 pages.

Fulton, et al., The Inability of a Bacterial Lipase Inhibitor to Control Acne Vulgaris, The Journal of Investigative Dermatology, vol. 64, Apr. 1975, Abstracts, 281.

Gump, et al., "Side Effects of Minocycline: Different Dosage Regimens," Antimicrobial Agents and Chemotherapy, 1977, 12, 642–646.

Healy, et al., "Acne vulgaris," Education & Debate, Fortnightly Review, BMJ, 1994, 308, 831–833.

Jacobson, et al., "Vestibular Reactions Associated with Minocycline," Antimicrobial Agents and Chemotherapy, 1975, 8, 4, 453–456.

Lawrenson, et al., "Liver damage associated with minocycline use in acne: a systemic review of the published literature and pharmacovigilance data," Drug Saf., 2000, 4, 333–49, abstract.

McGhee, et al., "Clinical utility of antinuclear antibody tests in children," BMC Pediatr., 2004, 4, 13, abstract.

Minocin Product Information, Lederle, 1134–1136.

Nacht et al., "Skin Hydration in Vitro: A Possible Role for Lipids," Journal of Investigative Dermatology, vol. 64, Apr. 1975, Abstracts, 281.

Ogden et al., Mean Body Weight, Height, and Body Mass Index, United States 1960–2002, Advance Data From Vital and Health Statistics, No. 347, Oct. 27, 2004.

Smith, et al., "Effect of Lipids on the Barrier Function of the Stratum Corneum," Federation Proceedings, Federation of American Societies for Experimental Biology, Feb. 1980, vol. 39, No. 2, abstract.

Tan, et al., "Range of antinuclear antibodies in healthy individuals," Arthritis Rheum. 1997, 40(9), 1601–11, abstract.

Agwuh, K.N. et al., "Pharmacokinetics of the tetracylines including glycylcyclines," J. Antimicrobial Chemotherapy, 2006, 58, 256–265.

Akamatsu, H. et al., "Increased hydrogen peroxide generation by neutrophils from patients with acne inflammation," Int. J. Dermatology, 2003, 42, 366–369.

American Hospital Formulary Service, 1996, AHFS Drug Information 96, p. 364.

American Hospital Formulary Service, AHFS Drug Information 1999, p. 430.

American Hospital Formulary Service, AHFS Drug Information 2003, pp. 446–448.

Arndt., K.A., et al., "Advances in Acne Research", Seminars in Cutaneous Medicine and Surgery, Jun. 2005, vol. 24, No. 2, 55 Pages.

Barringer, W.C. et al., "Minocycline hydrochloride and its relationship to other tetracycline antibiotics," Am. J. Pharm, Nov.–Dec. 1974, 179–191.

Bergfeld, W.F., "The Pathology of Acne Vulgaris in Children and Adolescents, Part 1", Cutis, 2004, 74, 92–97.

Bodokh, I., "Minocycline Induces an Increase in the Number of Excreting Pilosebaceous Follicles in Acne Vulgaris," Acta Derm Venereol. (Stockh) 1997, 77, 255–259.

Brinker, A., et al., "Trends in Adherence to a Revised Risk Management Program Designed to Decrease or Eliminate Isotretinoin–Exposed Pregnancies", Arch Derm., May 2005, vol. 141, 563–569.

Cartwright, A.C. et al., "A comparison of the bioavailability of minocycline capsules and film–coated tablets," J. Antimicrobial Chemotherapy, 1975, 1, 317–322.

Claussen, Von C.–F. et al., "Aequilibriometrische Messungen der zentralen Vestibularis–Dysregulation nach Gabe von Minocyclin," Arzneim–Forsch./Drug Res. 37 (II), Nr. 8, 1987 [English summary included].

Cordain, L. et al., "Acne Vulgaris,"Arch. Dermatol., Dec. 2002, 1584–1590.

Coskey, R.J., MD, Acne: Treatment with Minocycline, therapeutics for the clinician, Apr. 1976, 17, 799–801.

Cunliffe, W.J. et al., Letter to The Acne Support Group, titled: "The benefits/risks of Minocycline in the treatment of Acne" 1 page.

Davis, R.O., et al., "Consistency of Sperm Morphology Classification Methods", J. of Andrology, Jan./Feb. 1994, col. 15, No. 1, 83–91.

Del Rosso, J.Q., "A Qualitative and Quanitative Assessment of the Application and Use of Topical Acne Medication by Patients", Cutis, Drug Therapy Topics, Aug. 2005, vol. 76, 109–113.

Del Rosso, J.Q., "A Status Report on the Use of Subantimicrobial–Dose Doxycycline: A Review of the Biologic and Antimicrobial Effects of the Tetracyclines", Cutis, 2004, 118–122.

Del Rosso, J.Q., "Clinical Implications of Minocycline Use in Acne Vulgaris: Focus on Antimicrobial and Anti–inflammatory Properties," Cosmetic Dermatology, Aug. 2008, 21(8), 437–439.

Del Rosso, J.Q., et al., "What's New in the Medicine Cabinet?", Supplement to the Feb. 2005 Skin and Aging, 2005, 1–23.

Doyle, R.K., "Minocycline: Possible Vestibular Side–Effects," The Lancet, Oct. 19, 1974, p. 960.

Drew, T.M., et al., "Minocycline for Prophylaxis of Injection With Neisseria Meningitidis: High Rate of Side Effects in Recipients", Journal of Infectious Diseases, Feb. 1976, vol. 133, No. 2, 194–198.

Eady, E.A. et al., "Tetracycline–resistant propionibacteria from acne patients are cross–resistant to doxycycline, but sensitive to minocycline," British Journal of Dermatology, 1993, 128, 556–560.

Eady, E.A., "Bacterial Resistance in Acne", Dermatology, 1998, vol. 196, 59–66.

Eisen, D., et al., "Minocycline–Induced Pigmentation, Incidence, Prevention and Management", Drug Safety, 1998, 18 (6), 431–440.

Fanning, W.L., et al., "Side Effects of Minocycline: A Double–Blind Study", Antimicrobial Agents and Chemotherapy, Apr. 1977, 712–717.

Farrell, G.C., "Drug–induced hepatic injury," J. Gastroenterology and Hepatology, 1997, 12 (Suppl.), S242–S250.

FDA, Center for Drug Evaluation and Research, "Guidance for Industry—Evaluation of the Effects of Orally Inhaled and Intranasal Corticosteroids on Growth in Children", Nov. 2001, 12 Pages.

Federation of American Societies for Experimental Biology, "Epithelialion Transport", ABS, Feb. 1980, vol. 39, 106–110.

Frost, P., et al., "Phototoxic Potential of Minocycline and Doxycycline", Arch. Derm,, May 1972, vol. 105, 681–683.

Fulton, Jr., et al., "The Inability of a Bacterial Lipase Inhibitor to Control Acne Vulgaris", Journal Investigative Dermatology, 1975, vol. 64, 281, Abstract.

Gans, E.H., "Biotechnology Developments of Cosmetic Interest—An Evolving Review and Commentary," Cosmetics & Toiletries, Feb. 1988, 103, 37–48.

Goulden, V. et al., "Safety of long–term high–dose minocycline in the treatment of acne," British Journal of Dermatology, 1996, 134, 693–695.

Packman, E.W. et al., "Topical moisturizers: quantification of their effect on superficial facial lines," J. Soc. Cosmet. Chem., Feb. 1978, 29, 79–90.

"New Extended–Release Minocycline," Supplement to Cutis, Oct. 2008, vol. 78, No. 4S, 35 pages.

Alosh, M. et al., "Assessing the Relationship Between Investigator Global Evaluation and Acne Lesion Counts," Clinical and Nonclinical Drug Development, 2004, 38, 343–351.

Arbuckle, M. et al., "Development of Autoantibodies before the Clinical Onset of Systemic Lupus Erythematosus," New England Journal of Medicine, 2003, 349, 1526–1533.

Arora, S. et al., "Floating Drug Delivery Systems: A Review," AAPS PharmSciTech, 2005, 6(3), E372–E390.

Bergfeld, W. et al., Clinician: New Perspectives On Acne, 1996, 36 pages.

Berson, D. et al., "The treatment of acne: The role of combination therapies," Journal of the American Academy of Dermatology, 1995, 32, S31–S41.

Berthon, G. et al., "Metal Ion–Tetracycline Interactions in Biological Fluids. 2. Potentiometric Study of Magnesium Complexes with Tetracycline, Oxytetracycling, Doxycycline, and Minocycline, and Dicussion of their Possible Influence on the Bioavailability of these Antibiotics in Blood Plasma," Journal of Inorganic Biochemistry, 1983, 19, 1–18.

Bogentoft, C. et al., "Influence of Food on the Absorption of Acetylsalicylic Acid from Enteric–Coated Dosage Forms," European Journal of Clinical Pharmacology, 1978, 14, 351–355.

Bowles, W. et al., "The Effect of the Antioxidant Vitamin C on Minocycline–Induced Pigment Formation in Rats," Cosmetic Dermatology, 2004, 17(4), 215–218.

Bowles, W., "Protection against Minocycline Pigment Formation by Ascorbic Acid (Vitamin C)," Journal of Esthetic Dentistry, 10(4), 182–186.

Brogden R.N. et al., "Minocycline: A Review of its Antibacterial and Pharmacokinetic Properties and Therapeutic Use," Drugs, 1975, 9, 251–291.

Ceilley, R., "Advances in Topical Treatment of Acne and Rosacea," Journal of Drugs and Dermatology, 2004, 3(5), S12–S22.

Cheek, C.C. et al., "Dental and Oral Discolorations Associated with Minocycline and Other Tetracycline Analogs," Journal of Esthetic Dentistry, 1999, 11(1), 43–48.

Driscoll, M.S. et al., "Long–term oral antibiotics for acne: Is laboratory monitoring necessary?," Journal of the American Academy of Dermatology, 1993, 28, 595–602.

Eady, A.E. et al., "Is Antibiotic Resistance in Cutaneous Propionibacteria Clinically Relevant?: Implications of Resistance for Acne Patients and Prescribers," American Journal of Clinical Dermatology, 2003, 4(12), 813–831.

Elkayam, O. et al., "Clinical and Immunological Study of 7 Patients with Minocycline–induced Autoimmune Phenomena,"0 American Journal of Medicine, 1998, 105, 484–487.

Elkheshen, S. et al., "Per–oral Extended–Release Bioadhesive Tablet Formulation of Verapamil HCI," Bollettino Chimico Farmaceutico, 2003, 142(5), 226–231.

Feldman, S., et al., "Diagnosis and Treatment of Acne", American Family Physician, 2004, 69, 2123–2130.

Gans, E.H. et al., "A Study of Benzoyl Peroxide Gel Containing Zinc Lactate and Glycolic Acid for Treatment of Acne," Cosmetic Dermatology, 2002, 15(8), 33–36.

Gans, E.H. et al., "Comparative efficacy of clindamycin and benzoyl peroxide for in vivo suppression of *Propionibacterium acnes*," Journal of Dermatological Treatment, 2002, 13, 107–110.

Gans, E.H., "Polymer Developments of Cosmetic Interest", Cosmetics and Toiletries, 1988, 94–98.

Gans, E.H., "Why Natural?: Scientific Support of Natural Materials," Cosmetics & Toiletries, 1987, 102, 21–26.

Gans, E.H., "Working with Active Ingredients," Cosmetics & Toiletries, 1989, 104, 51–56.

Gans, E.H., et al., "In Vivo Determination of he Skin Atrophy Potential of the Super–High–Potency Topical Corticosteroid Fluocinonide 0.1% Cream Compared With Clobetasol Propionate 0.05% Cream and Foam and a Vehicle", Journal of Drugs in Dermatology, 2008, 7(1), 28–32.

Gans, E.H., et al., "The Solubility and Complexing Properties of Oxytetracycline and Tetracycline II.", Journal of the American Pharmaceutical Association, 1957, 587–589.

Gans, E.H., et al., "The Use of Polyethylene Glycol in Tablet Coating", Journal of the American Pharmaceutical Association, 1954, 483–485.

Gilbert, S.A. et al., "Extracellular Lipase(s) in *Corynebacterium Acnes*. I. Variation of Triglyceride Hydrolysis with Culture Age and Acyl Chain–Length,"Journal of Investigative Dermatology, 1974, 543.

Gordon, P.M. et al., "Minocycline–associated lupus erythematosus," British Journal of Dermatology, 1995, 132, 120–121.

Gough, A. et al, "Minocycline induced autoimmune hepatitis and systemic lupus erythematosus–like syndrome," British Medical Journal, 1996, 312, 169–172.

Gould, W.J. et al., "Minocycline Therapy," Archives of Otolaryngology, 1972, 96(3), 291.

Goulden, V. et al., "Safety of long–term high–dose minocycline in the treatment of acne," British Journal of Dermatology, 1996, 134, 693–695 (Abstract).

Gump, D.W., et al., "Side Effects of Minocycline: Different Dosage Regimens," Antimicrobial Agents and Chemotherapy, Nov. 1977, 642–646.

Guzick, D.S., et al., "Sperm Morphology, Motility, and Concentration in Fertile and Infertile Men", The New England Journal of Medicine, Nov. 2001, vol. 345, No. 19, 1388–1393.

Habif, T.P., Ch. 7, "Acne, Rosacea and Related Disorders" in Clinical Dermatology 4$^{th}$ Edition, 2004, © 2004 Mosby Inc.

Haider, A., et al., "Treatment of Acne Vulgaris", JAMA, 2004, 726–735.

Heng, P.W.S. et al., "Investigation of the influence of mean HPMC particle size and number of polymer particles on the release of aspirin from swellable hydrophilic matrix tablets," J. Controlled Release, 2001, 76, 39–49+.

Hui, X. et al., "Ciclopirox Delivery into the Human Nail Plate,"J. Pharmacological Sci, Oct. 2004, 93(10), 2545–2548.

Jacobson, J. et al., "Vestibular Reactions Associated with Minocycline," Antimicrobial Agents and Chemotherapy, Oct. 1975, 8(4), 453–456.

Jonas, M., et al., "Review Micocycline", Therapeutic Drug Monitoring, 1982, 4, 137–145.

Kligman, A.M., "Comparison of a topical peroxide gel, oral minocylcine, oral doxycycline and a combination for suppression of P. acnes in acne patients," J. Dermatological Treatment, 1998, 9, 187–191.

Kligman, L.H., et al., "Re–emergence of Topical Retinol in Dermatology", Journal of Dermatological Treatment, 2000, 11, 47–52.

Langevitz, P., et al., "Benefits and Risks of Minocycline in Rheumatoid Arthritis", Drug Safety, May 2000, 22(5), 405–414.

Layton, A.M., et al., "Minocycline Induced Pigmentation in the Treatment of Acne—A Review and Personal Observations", Journal of Dermatological Treatment, 1989, 9–12.

Layton, A.M., et al., "Phototoxic Eruptions Due to Doxycycline—A Dose–Related Phenomenon", Clinical Experimental Dermatology, 1993, 18, 425–427.

Lee, C.H., et al., "Characterization of In–Vitro Spermicidal Activity of Chelating Agent Against Human Sperm", Journal of Pharmaceutical Sciences, 1996, vol. 85, No. 6, 649–654.

Leyden, J. et al., "A systemic type I 5 alpha–reductase inhibitor is ineffective in the treatment of acne vulgaris," J. Am. Acad. Dermatol., 2004, 50, 443–447.

Leyden, J.J. et al., "The human in vivo antimicrobial effects of dual acne therapy: oral Dynacin® (minocyline HCl) plus topical Triaz (benzoyl peroxide special gel)," J. Dermatological Treatment, 1997, Suppl. 2, S3–S6.

Leyden, J.J., "New understandings of the pathogenesis of acne," J. Am. Acad. Dermatol., 1995, 32, S15–S25.

Leyden, J.L., "A Review of the Use of Combination Therapies for The Treatment of Acne Vulgaris", Journal American Academy Dermatology, 2003, 49, S200–S210.

Leyden, J.L., "Antibiotic Resistance in the Topical Treatment of Acne Vulgaris", Cutis, 2004, 73, (suppl 6), 6–10.

Leyden, J.L., "Effect of Topical Benzoyl Peroxide/Clindamycin Versus Topical Clindamycin and Vehicle in the Reduction of Propionibacterium Acnes", Therapeutics for the Clinician, 2002, vol. 69, 475–480.

Leyden, J.L., et al., "Topical Retinoids in Inflammatory Acne: A Retrospective, Investigator–Blinded, Vehicle–Controlled, Photographic Assessement", Clinical Therapeutics, 2005, vol. 27, No. 2, 216–224.

Lucky, A.W. et al., "A multirater validation study to assess the reliability of acne lesion counting," J. Am. Acad. Dermatology, Oct. 1996, 559–560.

Malcolm, A. et al., "Minocycline–Induced Liver Injury," Am. J. Gastroenterology, 1996, 91(8),, 1641–1643.

Marks, R. (Ed.), Journal of Dermatological Treatment, 1997, vol. 8, Supplement 2, S1–S10.

Nacht, S., et al., "Skin Friction Coefficient: Changes Induced by Skin Hydration and Emollient Application and Correlation with Perceived Skin Feel", J. Soc. Cosmet, Chem., 1981, 32, 55–65.

Nangia, A., "Bioadhesives for Targeted Oral Drug Delivery," Drug Delivery Report, Spring/Summer 2006, 25–32.

Nicol, C.S., et al., "Micocycline: Possible Vestibular Side–Effects", The Lancet, Nov. 1974, 1260.

Orris, L., et al., "Oral Zinc Therapy of Acne", Arch. Dermatol, 1978, vol. 114, 1018–1020.

Packman, E.W. et al., "The panel study as a scientifically controlled investigation: moisturizers and superficial facial lines," J. Soc. Cosmet. Chem., Feb. 1978, 29, 91–98.

Pauporte, M. et al., "Selegiline Transdermal System (STS): Assessments of Dermal Safety in Human," J. Toxicology, 2004, 23(3), 179–187.

Pollock, R.W., et al., "Pharmaceutical Patent and Exclusivity Complexity: Implications for Generic Product Introductions", Pharmacy Times, 2002, 70–79.

Raloff, "Sometimes an antibiotic is much more," Science News, Feb. 24, 2001, vol. 159, 115–117.

Rapp, D.A., et al., "Anger and Acne: Implications for Quality of Life, Patient Satisfaction and Clinical Care", Brit. Journal of Dermatology, 2004, 151(1), 183–189.

Ross, J.I., et al., "Phenotypic and Genotypic Characterization of Antibodtic–Resistant Propionibacterium Acnes Isolated From Acne Patients Attending Dermatology Clinics in Europe, The USA, Japan and Australia", Brit. Journal of Dermatology, 2001, 144, 339–346.

Schmidt, N.F. et al., "Demodex and Rosacea, II: Demodex Mites and Rosacea Inflammation," Cosmetic Dermatology, Sep. 2004, 17(9), 575–580.

Singh, B. et al., "Formulation and Optimization of Controlled Release Mucoadhesive Tablets of Atenolol Using Response Surface Methodology," AAPS Pharm Sci. Tech., 2006, 7(1), E1–E10.

Sklar, J.L. et al., "Evaluation of Triaz 10% Gel and Benzamycin in acne vulgaris," J. Determatological Treatment, 1996, 7, 147–152.

Smith, W.P. et al., "Effect of Lipids on the Aggregation and Permeability of Human Stratum Corneum," Journal of Investigative Dermatology, 1982, 78(1), 7–11.

Smolinksi, K.N. et al., "Acne update: 2004," Current Opinion in Pediatrics, 2004, 16, 385–391.

Somech, R. et al., "Complications of Minocycline Therapy for Acne Vulgaris: Case Reports and Review of the Literature," Pediatric Dermatology, 1999, 16(6), 469–472.

Stern, R.S., "The prevalence of acne on the basis of physical examination," J. Am Acad Dermatol, 1992, 26, 931–935.

Straughn, A.B. et al., "Bioavailability of Seven Furosemide Tablets in Man," Biopharmaceutics and Drug Disposition, 1986, 7(2), 113–120.

Tan, J.K.L., "Psychosocial Impact of Acne Vulgaris: Evaluating the Evidence," Skin Therapy Letters, 2004, 9(7), 1–3, 9.

Thevarajah, S. et al., "Trends in prescription of acne medication in the US: Shift from antibotic to non–antibiotic treatment," Journal of Dermatological Treatment, 2005, 16, 224–228.

Thiboutol, D., "New Treatments and Therapeutic Strategies for Acne," Arch Fam Med, Feb. 2000, 9, 179–187.

Thiboutol, D., "Regulation of Human Sebaceous Glands," Progress in Dermatology, Dec. 2003, 37(4), 1–12.

Velasco, M.V. et al., "Influence of drug:hydroxypropylmethylcellulose ratio, drug and polymer particle size and compression force on the release of diclofenac sodium from HPMC tablets," J. Controlled Release, 1999, 57, 75–85.

WHO laboratory manual for the examination of human semen and sperm–cervical mucus interaction, $4^{th}$ edition, 1999.

Yeung, D. et al., "High–performance liquid chromatographic determination of free resorcinol in plasma and in urine," Journal of Chromatography, 1981, 224, 513–518.

Yeung, D. et al., "Percutaneous Absorption, Blood Levels, and Urinary Excretion of Resorcinol Applied Topically in Humans," International Journal of Dermatology, 1983, 22(5), 321–324.

Abbitt, B., et al., "Effect of Dihydrostreptomycin or Oxytetracycline on Reproductive Capacity of Bulls", Amer. Journal Vet. Res., 1984, vol. 45, No. 11, 2243–2246.

Ad Hoc Committe Report, "Systemic Antibiotics for Treatment of Acne Vulgaris", Arch. Dermatology, 1975, vol. 111, 1630–1636.

Ahmad, K., et al., "Postthaw Survival and Fertility of Frozen Bull Spermatozoa Treated With Antibiotics and Detergent", J. Dairy Science, 69, 535–541.

Aventis Press Release, 2004, "Aventis Announces FDA Approval of KETEK (Telithromycin) Tablets", 2 pages.

Barth, A.D., et al., "The Effect of Streptomcyin, Oxytetracycline, Tilmicosin and Phenylbutazone on Spermatogenesis in Bulls", Con. Vet. J., 1998, vol. 39, 103–106.

Bernier, C., et al., Minocycline, Ann Dermatol Venereol, 2001, 128, 627–637.

Bompey, N., "Searching for the Elusive Fountain of Youth", Asheville Citizen–Times, 2007, 2 pages.

Coates, P., et al., "Prevalance of Antibiotic–Resistant Propionibacteria On The Skin of Acne Patients: 10–Year Surveillance Data and Snapshot Distribution Study", Brit. Journal of Dermatology, 2002, 146, 840–848.

D'Addario, S.F., et al., "Minocycline–Induced Immune Thrombocytopenia Presenting as Schamberg's Disease", J. Drugs Dermatol, 2003, 3, 320–323.

dePaz, S., et al., "Severe Hypersensitivity Reaction to Minocycline", Invest. Allergol Clin. Immunol, 1999, vol. 9(6), 403–404.

Dreno, B., et al., "Acne: Evolution of the Clinical Practice and Therapetuic Management of Acne Between 1996 and 2000", Eur. J. Dermatol., 2003, 13, 166–170.

Eady, A.E., et al., "Is Antibiotic Resistance in Cutaneous Propionibacteria Clinically Relevant?", American Journal Clinical Dermatology, 2003, 4(12), 813–831.

El–Hallak, M., et al., "Chronic Minocycline–Induced Autoimmunity in Children", Journal Peds., 2008, 314–319.

FDA, Federal Register, Aug. 2006, vol. 71, No. 167, 51146–51155, Skin Bleaching Drug Products For Over–The–Counter Human Use: Proposed Rule.

Goldstein, N.S., et al., "Minocycline as a Cause of Drug–Induced Autoimmune Hepatitis", Amer. J. Clin. Pathol., 2000, 114, 591–598.

Gordon, M.M., et al., "Minocycline Induced Lupus: Case Series in the West of Scotland", Journal Rheumatol., 2001, 28, 1004–1006.

Hargreaves, C.A., et al., "Effects of Co–Trimoxazole, Erythromycin, Amoxycillin, Tetracycline and Chloroquine or Sperm Function In Vitro", Human Reproduction, 1998, vol. 13, No. 7, 1878–1886.

Hudson, C.P., et al., "The Tetracycline—Oral Contraceptive Controversy", American Acad. Dermatology, 1982, 269–270.

Huntington Study Group, "Minocycline Safety and Tolerability in Huntington Disease", Neurology, 2004, 63, 547–549.

Johnson, B.A., et al., "Use of Systemic Agents in the Treatment of Acne Vulgaris"American Acad. of Family Physicians, 2000, vol. 62, No. 8, 12 pages.

Lawrenson, R.A., et al., "Liver Damage Associated with Minocycline Use in Acne", Drug Safety, 2000, 23(4), 333–349.

Leyden, J.L., et al., "Comparison of the Efficacy and Safety of a Combination Topical Gel Formulation of Benzoyl Peroxide and Clindamycin With Benzoyl Peroxide, Clindamycin and Vehicle Gel in the Treatments of Acne Vulgaris", American Journal Clinical Dermatology, 2001, 2(1), 33–39.

Margolis, D.J., et al., "Association of Lack of Association Between Tetracycline Class Antibiotics Used for Acne Vulgaris and Lupus Erythematosus", Brit. Journal of Dermatology, 2007, 1–7.

Marzo–Ortega, H., et al., "Is Minocycline Therapy in Acne Associated with Antineutrophil Cytoplasmic Antibody Positivity?—A Cross–Sectional Study", British Journal Dermatology, 2007, 156, 1005–1009.

Marzo–Ortega, H., et al., "Minocycline Induced Autoimmune Disease in Rheumatoid Arthritis: A Missed Diagnosis?", J. Rheumatology, 2001, 28, 377–378.

Medicis' Response to FDA's Mar. 22 and 29 Information Request, Solodyn, 2006, 5 pages.

Nyirady, J., et al., "A Comparative Trial of Two Retinoids Commonly Used in The Treatment of Acne Vulgaris", Journal of Dermatology Treatment, 2001, 12, 149–157.

Oddo, M., et al., "Relapsing Acute Respiratory Failure Induced by Minocycline", Chest, 2003, 123, 2146–2148.

Ogden, C.L., et al., "Mean Body Weight, Height and Body Mass Index, United States 1960–2002", CDC, Advance Data, Oct. 2004, No. 347, 46 pages.

Pastolero, G.C., et al., "Drug–Related Pigmentation of the Thyroid Associated with Papillary Carcinoma", Arch. Pathol. Lab. Med., 1994, 79–83.

Ross, J.I., et al., "Antibiotic–Resistant Acne: Lessons From Europe", Brit. Journal of Dermatology, 2003, 148, 467–478.

Saivin, S., et al., "Clinical Pharmacokinetics of Doxycycline and Minocycline", Clinical Pharmacokinetics, 1988, 15, 355–366.

Sethi, S., et al., "ANCA–Positive Crescentic Glomerulonephritis Associated with Minocycline Therapy", American Journal of Kidney Diseases, 2003, vol. 42, No. 2, 1–5.

Shalita, A., "The Integral Role of Topical and Oral Retinoids in the Early Treatment of Acne", JEADV, 2001, 15, (Suppl. 3), 43–49.

Shenfield, G.M., et al., "Clinical Pharmacokinetics of Contraceptive Steriods", Clinical Pharmacokinetics, 1991, 20(1), 15–37.

Sokolov, J.J., et al., "Isolation of Substances From Human Vaginal Secretions Previously Shown to be Sex Attractant Pheromones in Higher Primates", Archives of Sexual Behavior, 1976, vol. 5, No. 4, 269–274.

Strauss, J.S., "A Color Guide to Diagnosis and Therapy", Clinical Dermatology, 4$^{th}$ Edition, Chapter 26, 332–339.

Taurog, A., et al., "Minocycline and the Thyroid: Antithyroid Effects of the Drug, and the Role of Thyroid Peroxidase in Mlnocycline–Induced Black Pigmentation of the Gland", Thyroid, 1996, vol. 6, No. 3, 211–219.

Thieltz, A., et al., "Control of Microcomedone Formation Throughout a Maintenance Treatment with Adapalence Gel, 0.1%", JEADV, 2007, 21, 747–753.

Timmermans, L., "Influence of Antibiotics on Spermatogenesis", The Journal of Urology, 1974, vol. 112, 348–349.

Usatine, R.P., et al., "Pearls in the Management of Acne", Dermatology First Edition, Orkin–Ed., 15 pages.

Williamson, P., et al., "A New Method for the Quantitative Investigation of Cutaneous Bacteria", Journal of Investigative Dermatology, 1965, vol. 45, No. 6, 498–503.

Yoshiki Miyachi et al., "Effect of Antibiotics on the Generation of Reactive Oxygen Species", The Society for Investigative Dermatology, 1986, 449–453.

"Is Minocycline Overused in Acne?", DTB, 2006, vol. 44, No. 8, 60–62.

Antonov, D., et al., "Drug–Induced Lupus Erythematosus", Clinics in Dermatology, 2004, 22, 157–166.

Callen., J.P., "Minocycline and Lupis–Like Disease: How Concerned should Practitioners Be?", 3 Pages.

Champion. R.H., et al., "Disorders of the Sebaceous Glands", Textbook of Dermatology, Sixth Edition, vol. 3, Chapter 42.

Clindamycin and Tretinoin Therapy for Acne: "A Review of Their Anti–inflammatory Activities", 1–53.

Clinical Acne Reviews, "A Multi-Centered, Open-Label Investigation of Triaz (benzoyl peroxide) In The Treatment of Moderate Acne", 1999, vol. 1, 6 Pages.

Crittenden, R.G., et al., "Cow's Milk Allergy: A Complex Disorder", Journal of the American College of Nutrition, vol. 24, No. 6, 582S–591S.

Del Rosso, J.Q., "Benzoyl Peroxide Cleansers for the Treatment of Acne Vulgaris: Status Report on Available Data", Cutis, 2008, 82, 336–342.

Del Rosso, J.Q., "Extended–Release Minocycline Tablets", Medicis FYI, 2007, 2 Pages.

DelRosso, J.Q., "Weight–Based Dosing and Extended–Release Formulation of Minocycline Tablets", Journal Clinical Aesthetic Dermatology, 2009, 44–47.

DelRosso, J.Q., et al., "Use of Oral Doxycycline for Community–Acquired Methicillin–Resistant Staphylococcus Aureus (CA–MRSA) Infections", Journal Clinical Aesthetic Dermatology, 2009, 45–50.

Dermatology World, 2008, 24 Pages.

Eda, A., et al., "Acute Allergic Reaction Due to Milk Proteins Contaminating Lactose Added to Corticosteroid for Injection", Allergology International, 2009, 58, 137–139.

Eshki, M., et al., "Twelve–Year Analysis of Severe Cases of Drug Reaction With Eosinophilia and Systemic Symptoms", Arch Dermatol., 2009, vol. 145, No. 1, 67–72.

FDA–CDER, "Bioavailability and Bioequivalence Studies for Orally Administered Drug Products—General Considerations", Guidance For Industry, 2002, 27 Pages.

FDA–CDER, "Extended Release Oral Dosage Forms: Development, Evaluation, and Application of In Vitro/In Vivo Correlations", Guidance For Industry, 1997, 27 pages.

Gustaffson, C., et al., "Characteristics of Hydroxypropyl Methylcellulose Infljuencing Compactibility and Prediction of Particle and Tablet Properties by Infrared Spectroscopy", Jour. Pharma. Sciences, 2003, vol. 92, No. 3, 460–470.

Howard C. Ansel et al., eds., Pharmaceutical Dosage Forms and Drug Delivery Systems, 213–221, 1995.

Jemal, M., "High–Throughput Quantitative Bioanalysis by LC/MS/MS", Biomedical Chromatography, 2000, 14, 422–429.

Kamel, A., et al., "High Performance Liquid Chromatography/Atomospheric Pressure Ionization/Tandem Mass Spectrometry (HPLC/API/MS/MS) in Drug Metabolism and Toxicology", Current Drug Metabolism, 2006, 7, 837–852.

Kang, S.–W., et al., "A Case of Black Thyroid Associated with Hyalinizing Trabecular Tumor", Endocrine Journal, 2008, 55(6), 1109–1112.

Leyden, J.J., "Current Issues in Antimicrobial Therapy for the Treatment of Acne", JEADV, 2001, 15 (Suppl. 3), 51–55.

Leyden, J.J., et al., "Evaluation of the Antimicrobial Effects In Vivo of Triaz Gel (benzoyl peroxide special gel), Cleocin–T Lotion (clindamycin phosphate lotion), and Azelex Cream (azelaic acid cream) in Humans", Journal Dermatological Treatment, 1997, Supp. 2, S7–S10.

Leyden, J.J., Supplement to Cutis, Oct. 2006, vol. 78, No. 4S, 7 Pages.

Macdonald, H., et al., "Pharmacokinetic Studies on Minocycline in Man", Kinetics of Minocycline, 1973, 852–861.

Neergaard, L., "Compounds Could Slow Parkinson's Disease", AP Associated Press, Yahoo News, 2006, 2 Pages.

Neils, H.J.C.F., et al., "Metabolsim of Minocycline in Humans", Drug Metabolism and Disposition, 1982, vol. 10, No. 2, 142–147.

Nelis, H.J.C.F., et al., "Unique Metabolic Fate of a Tetracycline (Minocycline)", The Lancet, 1981, 938.

Plott, R.T. "Worldwide Literature Review of Minocycline Adverse Events in the Treatment of Acne and Non–Acne Indications", 2005, TOC and NDA–50–808, Solodyn Labeling Amendment.

Ruhe, J.J., et al., "Use of Long–Acting Tetracyclines for Methicillin–Resistant Staphylococcus Aureus Infections: Case Series and Review of the Literature", CID, 2005, 40, 1429–1434.

Sarzi–Puttini, P., et al., "Drug–Induced Lupus Erythematosus", Autoimmunity, 2005, 38, 7, 507–518.

Schlienger, R.G., et al., "Minocycline–Induced Lupus", Dermatology, 2000, 200, 223–231.

Springhouse Skin Research, "The Presence of Specific Follicular Fluorescence in Cyanoacrylate Biopsies From Subjects on Orally Administered Tetracyclines", 1977, 3 Pages.

Storm, A., et al., "One in 3 Prescriptions Are Never Redeemed: Primary Nonadherence in an Outpatient Clinic", Journal Academy Dermatology, 2008, 59, 27–33.

Study Report, "A Single Dose Four–Way Crossover Dose Proportionality Study of Minocycline Caplets in Healthy Volunteers", AAA–US–233, 6 Pages.

Tan, E.M., et al., "Range of Antinuclear Antibodies in "Healthy" Individuals", Arthritis and Rheum., 1997, 40(9), 1601–1611.

Toosi, P., et al., Subantimicrobial–dose Doxycycline in the Treatment of Moderate Facial Acne, 2008, vol. 7, Issue 12, 1149–1152.

vanSteensel, M.A.M., "Why Minocycline Can Cause Systemic Lupus—A Hypothesis and Suggestions for Therapeutic Interventions Based On It", Medical Hypothesis, 2004, 53, 31–34.

Viriden, A., et al., "Investigation of Critical Polymer Properties for Polymer Release and Swelling of HPMC Matrix Tablets", Journal of Pharmaceutical Sciences, 2009, 297–309.

Viriden, A., et al., "The Effect of Chemical Heterogeneity of HPMC on Polymer Release From Matrix Tablets", Eur. Journal of Pharmaceutical Sciences, 2008, 1–9.

Voils, S.A., et al., "Use of Macrolides and Tetracyclines for Chronic Inflammatory Diseases", Annals of Pharmacotherapy, 2005, vol. 39, 9 Pages.

Welling, P.G., et al., "Bioavailability of Tetracycline and Doxycycline in Fasted and Nonfasted Subjects", Antimicrobial Agents and Chemotherapy, 1977, vol. 11, No. 3, 462–469.

Xu, R.N., et al., "Recent Advances in High–Throughput Quantitative Bioanalysis by LC–MS/MS", Journal Pharmaceutical and Biomedical Analysis, 2007, 44, 432–355.

Donachie, R.J. et al., "A Comparison of the side effects producetd by Vectrin and Dynacin brands of minocycline HCL after normal dosage," Clinical Acne Reviews, vol. 2, Nov. 1997, 7 pages.

Adolfo C. Fernandez–Obregon, "Azithromycin for the treatment of acne," International Journal of Dermatology 2000, 39, 45–50.

Gans et al., The Solubility and Complexing properties of Oxytetracycline and Tetracycline II, Journal of the American Pharmaceutical Association, Sci. Ed. 46, No. 10, Oct. 1957.

Sheehan–Dare, et al., "A Double–blind Comparison of Topical Clindamycin and Oral Minocyclin in the Treatment of Acne Vulgaris", Acta Derm Venereol (Stockh), 70, pp. 534–537, 1990.

Ta et al., "Effects of Minocycline on the Ocular Flora of Patients with Acne Rosacea or Seborrheic Blepharitis," Cornea vol. 22(6): 545–548, 2003.

Piérard–Franchimont et al., 2002. "Lymecycline and Minocycline in inflammatory Acne." Skin Pharmacol. Appl. Skin Physiol., 15, 112–119.

AAI International PROSLO™ and PROSLO™ II Tablets Technology, referencing patents issued prior to 2000.

Aditya K. Gupta et al., Solodyn (Minocycline HCI, USP) Extended–Release Tablets, LE JACQ, 291–292, Nov. Dec. 2006.

AJ Darrah et al., "An open multicentre study to compare fusidic acid lotion and oral minocycline in the treatment of mild–to–moderate acne vulgaris of the face," European Journal of Clinical Research 8:97–107, 1996.

Allen N. Sapadin et al., "Tetracyclines: Nonantibiotic properties and their clinical implications," American Academy of Dermatology, Inc., 258–265, Feb. 2006.

Arndt et al., "What disorders present with inflamed skin?" Cutaneous Medicine and Surgery, An Integrated Program in Dermatology, vol. 1, 470–471, 1996.

Arnold et al., Andrews' Diseases of the Skin: Clinical Dermatology, 8th Edition, p. 254, 1990.

Bal L. Lokeshwar et al., "Inhibition of Cell Proliferation, Invasion, Tumor Growth and Metastasis by an Oral Non–Antimicrobial Tetracycline Analog (COL–3) in a Metastatic Prostate Cancer Model," International Journal of Cancer: 98, 297–309 (2002).

Barbara Fingleton, "CMT–3 CollaGenex," Current Opinion in Investigational Drugs, vol. 4, No. 12, 1460–1467, Dec. 2003.

Brigitte Dreno, "Multicenter Randomized Comparative Double–Blind Controlled Clinical Trail of the Safety and Efficacy of Zinc Gluconate versus Minocycline Hydrochloride in the Treatment of Inflammatory Acne vulgaris," Dermatology 203:135–140, 2001.

Champion et al., "Disorders of the Sebaceous Glands," Textbook of Dermatology, 6th Edition, vol. 3, pp. 1958–1961, 1998.

Charles G. Hubbell et al. "Efficacy of Minocycline Compared with Tetracycline in Treatment of Acne Vulgaris," Archives of Dermatology, vol. 118, 989–992, Dec. 1982.

Millar et al., "A general practice study investigating the effect of minocycline (Minocin) mg bd for 12 weeks in the treatment of acne vulgaris," The British Journal of Clinical Practice, vol. 41, No. 8, Aug. 1987, 882–886.

F. Smit, "Minocycline versus Doxycycline in the Treatment of Acne vulgaris," Dermatologica 157:186–190, 1978.

Falk Ochsendorf, "Systemic antibiotic therapy of acne vulgaris," Journal der Deutschen Dermatologischen Gesellschaft, 4:828–841, 2006.

Fleischer, A.B. et al. "Safety and Efficacy of a New Extended–Release Formulation of Minocycline,". Cutis 2006; 78 (suppl4):21–31.

Freedberg, et al., Fiztpatrick's Dermatology in General Medicine, 5th Edition, vol. 1, pp. 77–78, 1999.

Webster et al., "Suppression of Polymorphonuclear Leukocyte Chemotactic Factor Production in Propionibacterium acnes by Subminimal Inhibitory Concentrations of Tetracycline, Ampicillin, Minocycline, and Erythromycin," Antimicrobial Agents and Chemotherapy, vol. 21, No. 5, May 1982, pp. 770–772.

Garner, S.E. et al., "Minocycline for Acne Vulgaris: Efficacy and Safety," (Cochrane Review), In: The Cochrane Library, issue 1, 2003, Chichester, UK: John Wiley & Sons, Ltd.

Webster, "Inflammation in acne vulgaris," Journal of the American Academy of Dermatology, vol. 33, No. 2, part 1, Aug. 1995, 248–253.

H. Akamatsu et al., "Effects of subminimal inhibitory concentrations of minocycline on neutrophil chemotactic factor production in comedonal bacteria, neutrophil phagocytosis and oxygen metabolism," Archives of Dermatological Research, 1991, 283: 524–528.

Hirohiko Akamatsu et al., "Effect of Doxycycline on the Generation of Reactive Oxygen Species," Acta Derm Venereol (Stockholm), 1992; 72: 178–179.

Japanese Publication No. JP 2076874 A; "Compounds Having Retinoid Like Activity and Pharmaceutical Composition Containing the Same". Published on Mar. 16, 1990, to Allergan, Inc.

James Q. Del Rosso, Clinical Significance of Brand Versus Generic Formulations: Focus on Oral Minocycline, Cutis, vol. 77, 153–156, Mar. 2006.

James Q. Del Rosso, et al. "Weight–based Dosing of a Novel Antibiotic for Moderate–to–Severe Acne Vulgaris Offers Potential for Improved Safety and Tolerability," www.millennium.com/ao/acne, Millennium CME Institute, Inc., 2006.

Jing Li et al, "Evidence for Dissolution Rate–Limited Absorption of COL–3, a Matrix Metalloproteinase Inhibitor, Leading to the Irregular Absorption Profile in Rats after Oral Administration," Pharmaceutical Research, Vo. 19, No. 11, 1655–1622, Nov. 2002.

Joseph B. Bikowski, "Treatment of Rosacea With Doxycycline Monohydrate," Therapeutics for the clinician, vol. 66, Aug. 2000, 149–152.

K Freeman, "Therapeutic focus, Minocycline in the treatment of acne," British Journal of Clinical Pharmacology, vol. 23, 112–123, Mar. 1989.

Kjell Hersle et al., "Minocycline in Acne Vulgaris: A Double–Blind Study," Current Therapeutic Research Vo, 19. No. 3, 339–342, Mar. 1976.

L. Illig, "Positive Side Effects of Antibiotic and Antimicrobial Substances in Therapy," Infection, vol. 7, Suppl. 6 (1979) pp. S584–588 (with English language summary).

Lorne M. Golub et al., "Tetracyclines Inhibit Connective Tissue Breakdown: New Therapeutic Implications for an Old Family of Drugs," Critical Reviews in Oral Biology and Medicine, 2(2): 297–322 (1991).

M. Schach Von Wittenau et al., "The distribution of Tetracyclines in Tissues of Dogs After Repeated Oral Administration," The Journal of Pharmacology and Experimental Therapeutics, vol. 152, 164–169, 1966.

Murray Jonas et al., "Minocycline," Therapeutic Drug Monitoring, 4:137–145, 1982.

Muzharul M. Islam, "A Nonantibiotic Chemically Modified Tetracycline (CMT–3) Inhibits intimal Thickening," American Journal of Pathology; vol. 163, No. 4, 1557–1566, Oct. 2003.

P.V. Harrison, "A comparison of doxycycline and mynocycline in the treatment of acne vulgars," Clinical and Experimental Dermatology 13:242–244, 1988.

Plott, R. T. and Wortzman, M., "Key Bioavailability Features of a New Extended–Release Formulation of Minocycline Hydrochloride Tablets," Cutis 2006; 78 (suppl4):6–10.

R. G. Kelly et al., "Metabolism and Tissue Distribution of Radioisotopically Labeled Minocycline," Elsevier, Toxicology and Applied Pharmacology 11, 171–183, 1967.

Richard E. B. Seftor et al, "Chemically modified tetracyclines inhibit human melanoma cell invasion and metatasis," Clinical & Experimental Metastasis, vol. 16, No. 3, 217–225 (1998).

Solodyn (Minocycline HCI Extended Release Tablets) Labeling and package insert Information, submitted with a New Drug Application approved May 8, 2006.

Stewart, D.M. et al. "Dose Ranging Efficacy of New Once–Daily Extended–Release Minocycline for Acne Vulgaris." Cutis 2006; 78 (suppl 4):11–20.

Stuart I. Brown et al., "Diagnosis and Treatment of Ocular Rosacea," Official Journal of the American Academy of Ophthalmology, vol. 85, Aug. 1977, 779–786.

Minocin product insert, Wyeth Pharmaceuticals Inc. Rev 10/05.

MinoPAC product information, Monthly prescribing Reference (Oct. 2006) and the product information (Aug. 2007).

Physician's Desk Reference; MINOCIN®: Minocycline Hydrochloride for Oral Use; Physician's Desk Reference, 1989, pp. 1134–1136, 43rd Edition; Edward R. Barnhard, publisher, Medical Economics Co., Inc.; Oradell, NJ.

Gollnick, Harald, et al., "Management of Acne, A Report From a Global Alliance to Improve Outcomes in Acne", Supplement to Journal of the American Academy of Dermatology, Jul. 2003, vol. 49, No. 1, SI–38.

Leyden, James J., "Absorption of Minocycline Hydrochloride and tetracycline hydrochloride", J. Am. Acad. Dermatol. 12:308–312, 1985.

Smith, Kelly, at al., "Safety of Doxycycline and Minocycline: A Systematic Review", Clinical Therapeutics, The international Peer–Reviewed Journal of Drug Therapy, vol. 27, No. 9, Sep. 2005, 1329–1342.

Williams D. N., et al., Minocycline: Possible vestibular side–effects. Lancet. Sep. 28, 1974;2(7883):744–6.

Leyden, James J., et al., "Comparison of Tazarotene and Minocycline Maintenance Therapies in Acne Vulgaris", Archives of Dermatology, May 2006, 605–612.

Leyden, James J., et al., "The antimicrobial effects in vivo of minocycline, doxycycline and tetracycline in humans", The Journal of Dermatological Treatment, Dec. 1996, vol. 7, No. 4, 223–225.

Leyden, James J., et al., "Tetracycline and Minocycline Treatment, Effects on Skin–Surface Lipid Levels and Propionibacterium acnes", Archives of Dermatology, 1982, vol. 118, 19–22.

Leyden, James J., et al., "Pseudomonas aeruginosa Gram–Negative Folliculitis", Archives of Dermatology, 1979, vol. 115, 1203–1204.

Leyden, James J., et al., "Clinical Considerations in the Treatment of Acne Vulgaris and Other Inflammatory Skin Disorders: Focus on Antibiotic Resistance", Cutis 2007 (suppl. 6), vol. 79, No. 65, 9–25.

Leyden, J., Introduction. Cutis 2006; 78 (suppl 4):4–5.

Marks, Ronald, et al., (eds.) "Dermatologic Therapy in Current Practice", Chapter 3, 35–44 (2002).

American Hospital Formulary Service Drug Information 88, 1988, 330–331.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-2, 5-11 and 14-18 are cancelled.

Claims 3-4 and 12-13 are determined to be patentable as amended.

New claims 19-34 are added and determined to be patentable.

3. [The method of claim 2] *A method for reducing the incidence or severity of vestibular side effects resulting from the treatment of acne by the use of oral minocycline, comprising administering the minocycline in a slowly dissolving dosage form*, wherein the [antibiotic] *minocycline* dissolves at a rate no faster than 15 percent in 15 minutes, 35 percent in 30 minutes, 50 percent in 45 minutes and 80 percent in 60 minutes.

4. [The method of the claim 2] *A method for reducing the incidence or severity of vestibular side effects resulting from the treatment of acne by the use of oral minocycline, comprising administering the minocycline in a slowly dissolving dosage form* wherein the [antibiotic] *minocycline* dissolves at a rate no faster than 20 percent in 15 minutes, 50 percent in 30 minutes, and 75 percent in 45 minutes.

12. [The method of claim 11] *A method for reducing the incidence or severity of vestibular side effects resulting from the treatment of acne by the use of oral minocycline, comprising administering the minocycline in a slowly dissolving dosage form*, wherein the dissolution of the minocycline is substantially complete in less than 24 hours, wherein the [antibiotic] *minocycline* dissolves at a rate no faster than 15 percent in 15 minutes, 35 percent in 30 minutes, 50 percent in 45 minutes and 80 percent in 60 minutes.

13. [The method of claim 11] *A method for reducing the incidence or severity of vestibular side effects resulting from the treatment of acne by the use of oral minocycline, comprising administering the minocycline in a slowly dissolving dosage form*, wherein the dissolution of the minocycline is substantially complete in less than 24 hours, wherein the [antibiotic] *minocycline* dissolves at a rate no faster than 20 percent in 15 minutes, 50 percent in 30 minutes, and 75 percent in 45 minutes.

*19. A method for reducing the incidence or severity of vestibular side effects resulting from the treatment of acne by the use of oral minocycline, comprising administering the minocycline once a day for multiple days in a dosage form that is slowly dissolving as measured under standard U.S. Pharmacopeia test conditions, wherein the minocycline dissolves at a rate no faster than 15 percent in 15 minutes, 35 percent in 30 minutes, 50 percent in 45 minutes and 80 percent in 60 minutes.*

*20. The method of claim 19 further comprising identifying at least one person susceptible to said effects prior to administering the minocycline to said at least one person.*

*21. A method for reducing the incidence or severity of vestibular side effects resulting from the treatment of acne by the use of oral minocycline, comprising administering the minocycline once a day for multiple days in a dosage form that is slowly dissolving as measured under standard U.S. Pharmacopeia test conditions, wherein the minocycline dissolves at a rate no faster than 20 percent in 15 minutes, 50 percent in 30 minutes, and 75 percent in 45 minutes.*

*22. The method of claim 21 further comprising identifying at least one person susceptible to such said effects prior to administering the minocycline to said at least one person.*

*23. A method for reducing the incidence or severity of vestibular side effects resulting from the treatment of acne by the use of oral minocycline, comprising administering the minocycline once a day for multiple days in a dosage form that is slowly dissolving as measured under standard U.S. Pharmacopeia test conditions, wherein the minocycline dissolves at a rate no faster than 15 percent in 15 minutes, 35 percent in 30 minutes, 50 percent in 45 minutes and 80 percent in 60 minutes, and wherein the dissolution of the minocycline is substantially complete in less than 24 hours.*

*24. The method of claim 23 further comprising identifying at least one person susceptible to such said effects prior to administering the minocycline to said at least one person.*

*25. A method for reducing the incidence or severity of vestibular side effects resulting from the treatment of acne by the use of oral minocycline, comprising administering the minocycline once a day for multiple days in a dosage form that is slowly dissolving as measured under standard U.S. Pharmacopeia test conditions, wherein the minocycline dissolves at a rate no faster than 20 percent in 15 minutes, 50 percent in 30 minutes, and 75 percent in 45 minutes, and wherein the dissolution of the minocycline is substantially complete in less than 24 hours.*

*26. The method of claim 25 further comprising identifying at least one person susceptible to such said effects prior to administering the minocycline to said at least one person.*

*27. A method for reducing the incidence or severity of vestibular side effects resulting from the treatment of acne by the use of oral minocycline, comprising administering the minocycline in a slowly dissolving dosage form, wherein the minocycline dissolves at a rate no faster than 15 percent in 15 minutes, 35 percent in 30 minutes, 50 percent in 45 minutes and 80 percent in 60 minutes, as measured under standard U.S. Pharmacopeia test conditions.*

*28. The method according to claim 27 further comprising identifying at least one person in need of treatment for acne prior to administering the minocycline to said at least one person.*

*29. A method for reducing the incidence or severity of vestibular side effects resulting from the treatment of acne by the use of oral minocycline, comprising administering the* minocycline in a slowly dissolving dosage form, wherein the minocycline dissolves at a rate no faster than 20 percent in 15 minutes, 50 percent in 30 minutes, and 75 percent in 45 minutes, as measured under standard U.S. Pharmacopeia test conditions.

30. The method according to claim 29 further comprising identifying at least one person in need of treatment for acne prior to administering the minocycline to said at least one person.

31. A method for reducing the incidence or severity of vestibular side effects resulting from the treatment of acne by the use of oral minocycline, comprising administering the minocycline in a slowly dissolving dosage form, wherein the dissolution of the minocycline is substantially complete in less than 24 hours, wherein the minocycline dissolves at a rate no faster than 15 percent in 15 minutes, 35 percent in 30 minutes, 50 percent in 45 minutes and 80 percent in 60 minutes, as measured under standard U.S. Pharmacopeia test conditions.

32. The method according to claim 31 further comprising identifying at least one person in need of treatment for acne prior to administering the minocycline to said at least one person.

33. A method for reducing the incidence or severity of vestibular side effects resulting from the treatment of acne by the use of oral minocycline, comprising administering the minocycline in a slowly dissolving dosage form, wherein the dissolution of the minocycline is substantially complete in less than 24 hours, wherein the minocycline dissolves at a rate no faster than 20 percent in 15 minutes, 50 percent in 30 minutes, and 75 percent in 45 minutes, as measured under standard U.S. Pharmacopeia test conditions.

34. The method according to claim 33 further comprising identifying at least one person in need of treatment for acne prior to administering the minocycline to said at least one person.

* * * * *